(12) United States Patent
Berman et al.

(10) Patent No.: US 6,748,250 B1
(45) Date of Patent: Jun. 8, 2004

(54) METHOD AND SYSTEM OF MONITORING A PATIENT

(75) Inventors: Herbert L. Berman, Los Altos Hills, CA (US); Robert N. Blair, San Jose, CA (US); James W. Moyer, San Francisco, CA (US)

(73) Assignee: Medoptix, Inc., Cupertino, CA (US)

( * ) Notice: Subject to any disclaimer, the term of this patent is extended or adjusted under 35 U.S.C. 154(b) by 26 days.

(21) Appl. No.: 09/844,687

(22) Filed: Apr. 27, 2001

(51) Int. Cl.[7] ............................................... A61K 9/22
(52) U.S. Cl. .................... 600/310; 600/316; 600/322; 128/903; 128/920; 702/188
(58) Field of Search ................................ 600/310, 504, 600/316, 508, 322; 607/30–32, 27, 14, 59; 128/903, 920; 604/50, 66, 67; 702/188, 127

(56) References Cited

U.S. PATENT DOCUMENTS

| | | | | |
|---|---|---|---|---|
| 5,607,460 A | * | 3/1997 | Kroll et al. ................... 607/30 |
| 5,666,956 A | * | 9/1997 | Buchert ....................... 128/664 |
| 5,857,462 A | * | 1/1999 | Thomas et al. ............. 128/633 |
| 6,049,727 A | * | 4/2000 | Crothall ....................... 600/310 |
| 6,249,705 B1 | * | 6/2001 | Snell ............................ 607/59 |
| 6,366,871 B1 | * | 4/2002 | Geva ........................... 702/188 |
| 6,409,675 B1 | * | 6/2002 | Turcott ....................... 600/508 |
| 6,418,346 B1 | * | 7/2002 | Nelson et al. ................ 607/59 |

* cited by examiner

Primary Examiner—Mark Paschall
(74) Attorney, Agent, or Firm—Fernandez & Associates, LLP

(57) ABSTRACT

A patient monitor system implemented by a service provider for users via recording a patient's analytes measurements by an attenuated total reflection (ATR) infrared total spectroscopy method. The system comprises an input module that provides a non-invasive method in measuring analytes in a patient, such as a measurement of the glucose level and other blood analytes. The measurement is shared among a plurality of output devices such as computers, personal digital assistants (PDAs), cellular phones, and pagers that are stationed or held by various users, such as doctors, patients, researchers, pharmacies, labs, and health insurers. In addition, behavioral attributes are recorded and correlated with the analytes measurements to generate a profile. The profile is selectively sent to output devices based on the user profile corresponding to the output device. Also, access to the profile is monitored by a security module that encrypts the profile to prevent access by un-authorized users.

27 Claims, 5 Drawing Sheets

METHOD AND SYSTEM OF MONITORING A PATIENT

BACKGROUND INFORMATION

1. Field of the Invention

The invention relates in general to devices and methods for improving the delivery of patient information and care to patients, particularly to transactions involved in utilizing a non-invasive monitoring system to deliver physiological information to patients and patients' service providers.

2. Description of Related Art

Numerous diseases require the monitoring of various physiological attributes of a patient. These attributes such as blood glucose level and other blood analytes' level are invaluable to patients and health service providers such as doctors, medical professions, pharmacies, researchers, insurance companies, and government agencies.

Particularly in patients with diabetes, monitoring the level of blood glucose is extremely important in controlling the patient's health, and decreasing or delaying the damaging effects of uncontrolled blood glucose. Diabetes is a disease in which the body does not produce or properly use insulin, which results in the increase uptake of glucose from the blood across cell membranes. About sixteen million people in the United States are diabetics. The American Diabetes Association reports that diabetes is the seventh leading cause of death in the United States. The complications of the disease include blindness, kidney disease, nerve disease, heart disease, and death.

Specifically, for diabetes, monitoring various physiological attributes is essential for diabetic patients. For example, it is essential that patients practice frequent self-monitoring of blood glucose (SMBG). Based upon the level of glucose in the blood, individuals may make insulin dosage decisions before injection. Monitoring the trends in blood glucose over time provides health care providers with invaluable information on the adequacy of therapy, the compliance of the patient and the progression of the disease. However, the prior systems of glucose monitoring usually requires obtaining blood from a finger stick (invasive method) or obtaining body fluids (other than blood) and subcutaneous tissue (also an invasive method). Now, an optical non-invasive glucose monitoring system, as illustrated in a related co-pending U.S. patent application entitled "Infrared ATR Glucose Measurement System (II)," U.S. application Ser. No. 09/547,433, by Herbert L. Berman and Jeffrey N. Roe, owned by the assignee of this application and incorporated herein by reference, provides a solution for non-invasively gathering of blood glucose information for diabetic patients. Use of a non-invasive technology rather than an invasive technology permits a significantly better approximation to continuous monitoring, which in turn may contribute significantly to improved health care for diabetic patients.

Therefore, it is advantageous to have a monitoring system that leverages on the non-invasive glucose-measuring device to provide a medium for sharing of the monitored information.

DETAILED DESCRIPTION OF PREFERRED EMBODIMENT

Reference is made in detail to embodiments of the invention. While the invention is described in conjunction with the embodiments, the invention is not intended to be limited by these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, as is obvious to one ordinarily skilled in the art, the invention may be practiced without these specific details. In other instances, well-known methods, procedures, and components have not been described in detail so that aspects of the invention will not be obscured.

Figure 1:
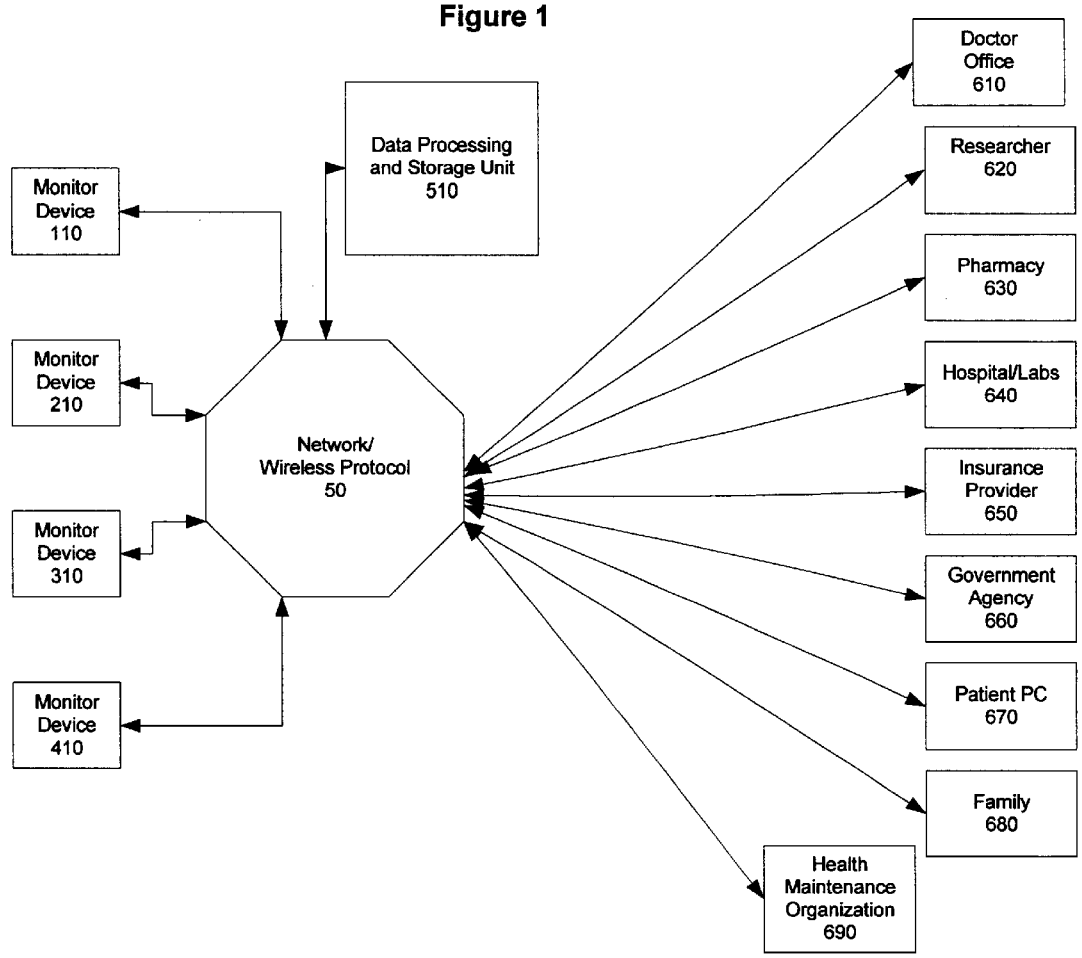
FIG. 1 is a block diagram of a monitor system according to the present invention.

Referring to FIG. 1, the elements of the patient monitoring system in accordance with one embodiment of the invention consist one or more non-invasive analyte monitor devices (110 210 310 410), a data processing and storage unit 510, and one or more information recipients 600, such as doctor office 610, researcher 620, pharmacy 630, hospital/labs 640, insurance provider 650, government agency 660, patient 670, family member 680, and health maintenance organization 690. All elements of the system can communicate with each other via a network or wireless protocol 50.

Figure 2:
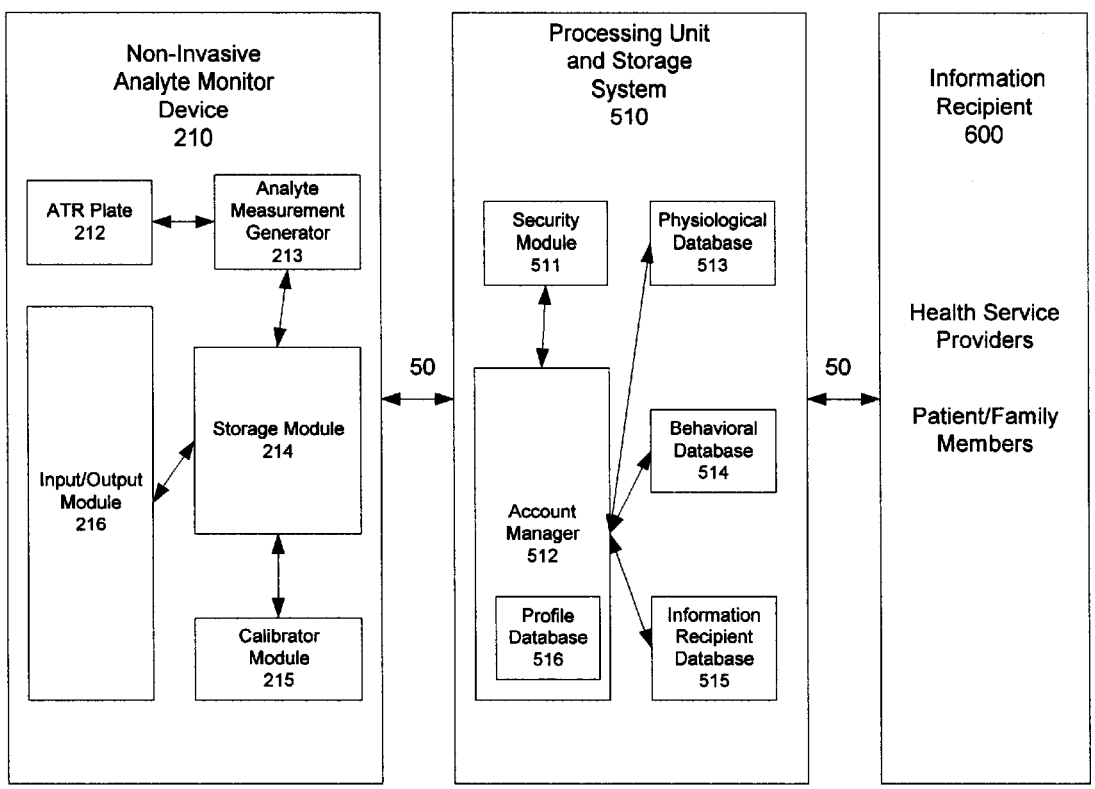
FIG. 2 illustrates a more detail illustration of the internal architecture of a non-invasive monitor device 210, a processing unit and storage system 510, and information recipients 600.

As illustrated in more detail in FIG. 2, the data processing and storage unit 510 implements for a user a monitoring system that organizes and processes physiological and behavior attributes of the user to enable transmission of these attributes to information recipients 600. The term "information recipients" as defined herein are person, organization, and corporation that are interested in the attributes gathered by the non-invasive analyte monitor device such as doctor office 610, researcher 620, pharmacy 630, hospital/labs 640, insurance provider 650, government agency 660, patient 670, family member 680, and health maintenance organization 690. Optionally, the data processing and storage unit can be programmed to send automated warnings such as by email, phone, or fax to a patient or information recipients if the patient's condition falls outside an acceptable limit that can be prescribed by the patient's caregiver or physician.

In one embodiment of the system where the user is a diabetic patient, the user utilizes the non-invasive analyte monitor device 210 based on attenuated total reflection (ATR) technology to measure blood glucose level. The analyte monitor device comprises an ATR plate 212 coupled to an analyte measurement generator 213, which calculates the blood glucose level on user's skin that is placed on the ATR plate 212 for measurement. The measurement is then stored in a storage module 214, which also can store other user information. The analyte device 210 requires calibration, which is accomplished by a calibrator module 215 that correlates the measurements generated from the analyte measurement generator 213 to measurements taken from standard invasive procedures such as a finger stick. After calibration, the analyte device 210 can be used to obtain accurate glucose level measurements without any other invasive procedures. The input/output module 216 allows the user to input information and also receive the analyte measurements from the measurement generator 213 or the storage module 214.

In an alternative embodiment, the user, via the input/output module 216, may also input behavior attributes such as "time duration between analyte measurement and last meal," "time duration between analyte measurement and last exercise session," "time duration between analyte measurement and last resting session, or "time and dosage of medication taken." These behavior attributes affect the interpretation of the blood glucose measurement. For example, blood glucose level tends to be higher for users that have just eaten a meal. Thus, by adding behavior attributes, the monitor system can provide a better profile of the user's health to information recipients 600 such as the user's doctor 610. Also, the user utilizes the input/output module 216 to include other physiological attributes such as heart rate or blood pressure. Optionally, the input/output module 216 can comprise an activity sensor that determines energy use and/or a metabolic activity sensor that measures metabolic rates such as oxygen consumption.

Additionally, the output module 216 of the analyte device 210 serves as a messaging terminal for the patient. These messages can be automatic alarms that alert the patient when the analyte measurements, behavior attributes, and physiological attributes are out of a normal range prescribed by the patient, the patient's caregiver, and/or the patient's physician. These messages can be generated by the analyte device itself or from any one of the information recipients. For example, if the patient's physician determines that the patient is not responding to a prescribed medicine dosage, the physician can send a message to the output module 216 to request the patient to change his dosage or to request a visit to the physician's office for consultation.

Figure 5:
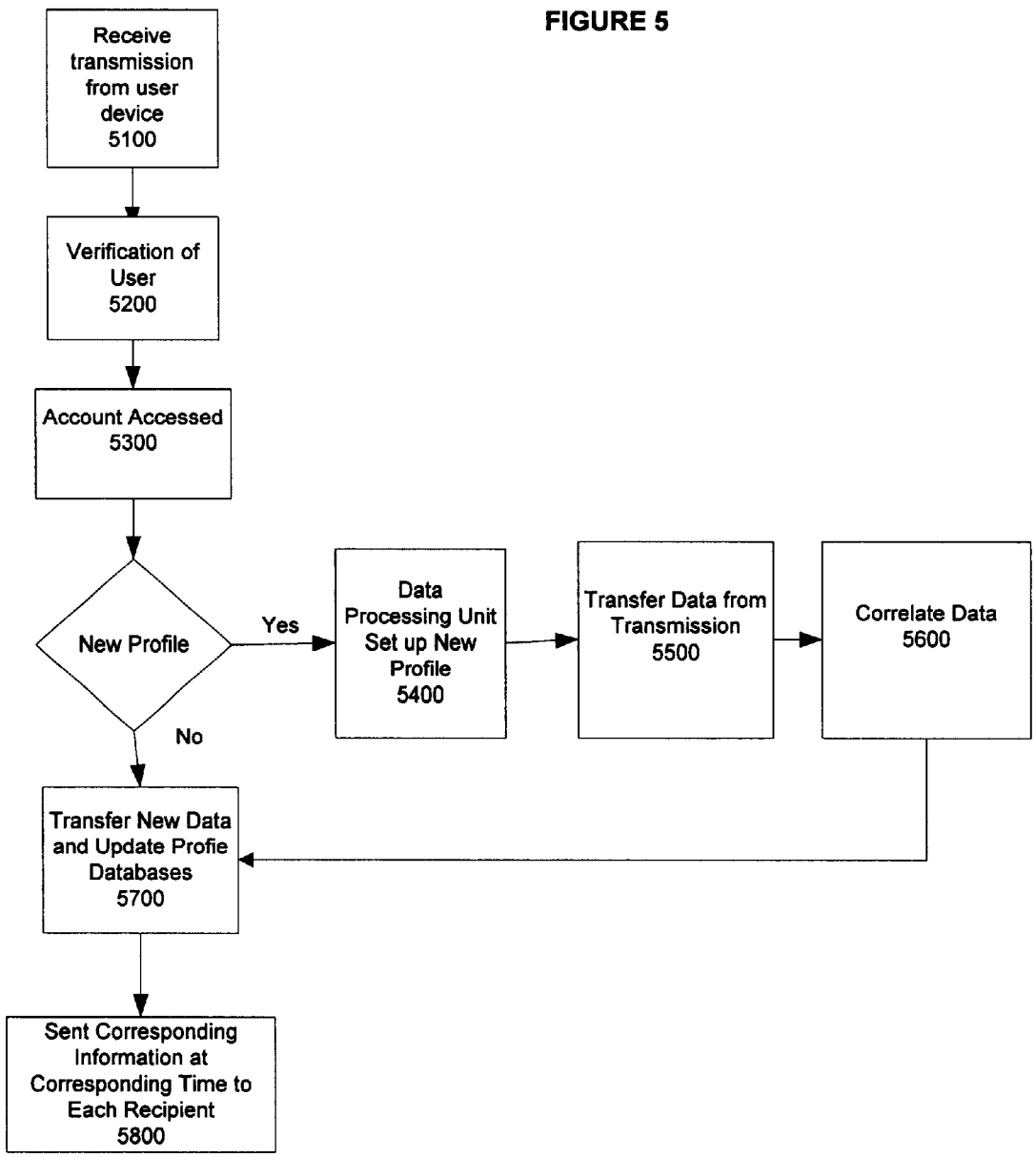
FIG. 5 is a flow chart of the information processing in a data processing unit.

All the analyte measurements, behavior attributes, and physiological attributes are communicated to the data processing and storage unit 510 for processing and storage, which will be furthered described in detail in FIG. 5. These attributes are sent to the data processing and storage unit 510 via a network such as the Internet, local area network (LAN) and/or wide area network (WAN), wireless and/or wired, or other network infrastructure 50. In one embodiment of the invention, the monitor device 210 has its own wireless transmission module. In an alternative embodiment of the wireless transmission, the monitor device 210 is coupled to a wireless device such as a cellular phone, a pager or a wireless modem to enable transmission. Optionally, due to the large amount of data being collected, the monitor device 210 may send all information to a local terminal and storage located within a patient's home, a physician's office, or a hospital. The information to the local terminal can be transmitted over a short-range radio frequency (RF) link (e.g. Blue tooth). Subsequently, the information stored at the local terminal will be communicated to the processing unit 510.

After communication is established between the monitor device 210 and the processing unit 510, an account manager 512 in the processing unit 510 accesses the user's account and the security module 511 verifies the user's identity via a password or any other security means. After verification, the attributes are transmitted and organized into a physiological database 513, which stores the user's analyte measurements and other physiological attributes, and a behavioral database, which stores the user's behavioral attributes. The account manager 512 also communicates with an information recipient database 515 that includes the user's selected information recipients 600 and recipient parameters associated with each specific information recipient. These "recipient parameters" as described herein are requirements that direct the transmission of the user attributes, which may include "type of information" such as report of blood glucose level, an email to alert if blood glucose level reaches a certain maximum or minimum, a report of behavioral and blood glucose correlation, "time of information" such as weekly, monthly, or quarterly, "format type" such as a graphical representation or text, and "information recipient" such as sending the information to doctor and patient personal computer, or sending to family members in case of emergency.

Figure 3:
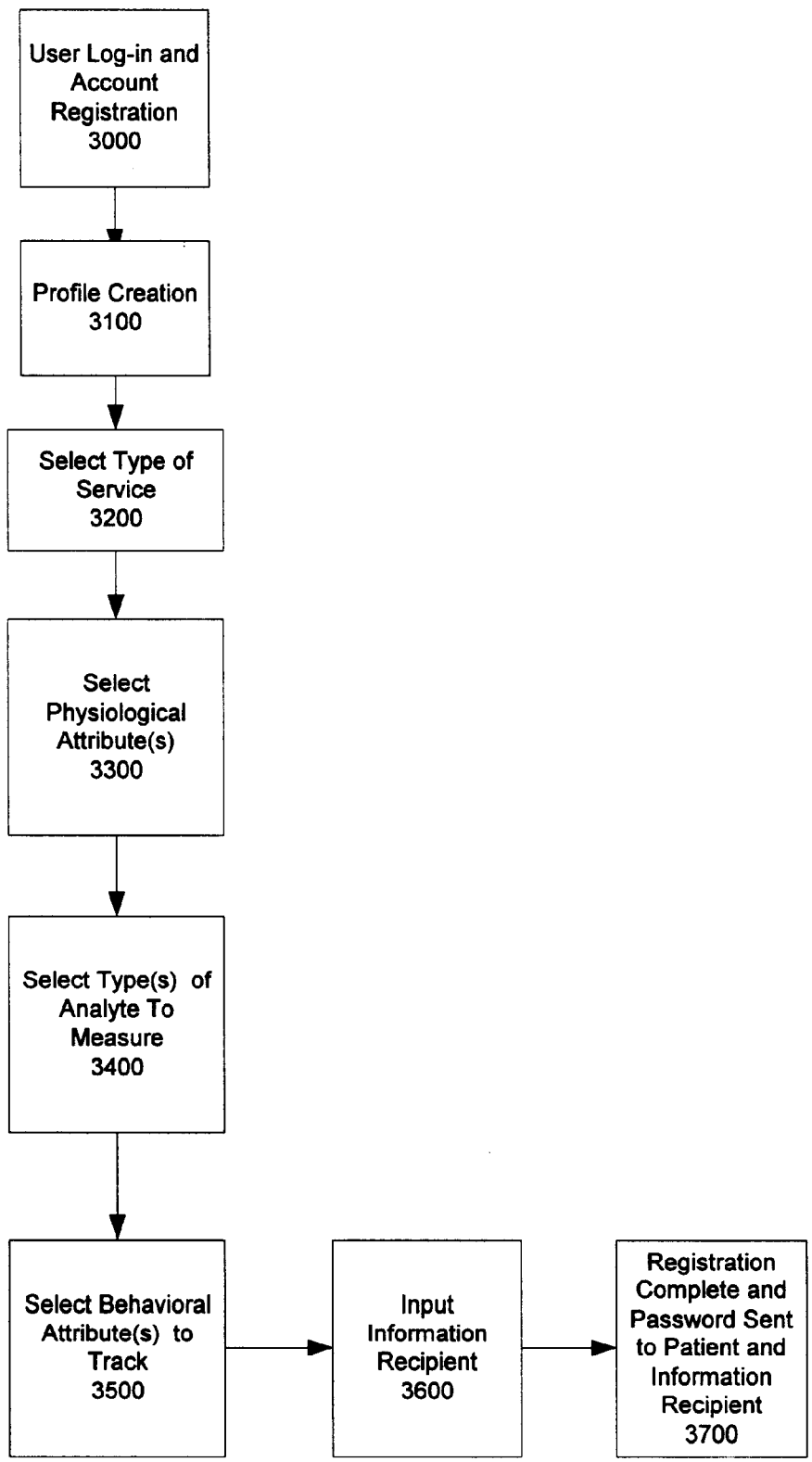
FIG. 3 illustrates a flow chart of registering information into the monitor device.
Figure 4:
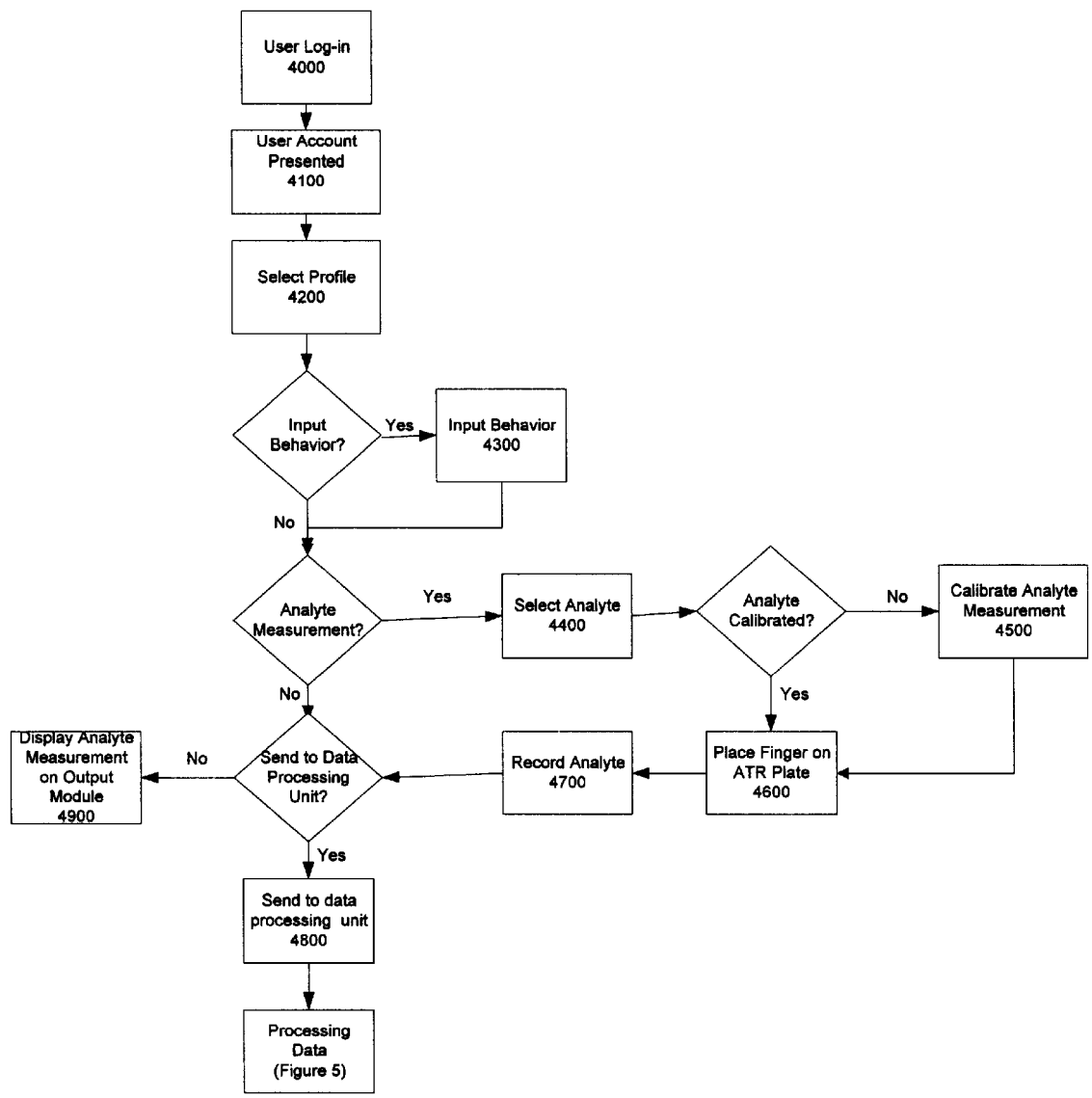
FIG. 4 illustrates the step-by-step information flow from the monitor device to a data processing and storage system.

The processes of gathering the user's attributes, processing the attributes, and transmitting the attributes to corresponding information recipients are furthered described in detail in FIG. 3, which illustrates the registration of the user, in FIG. 4, which illustrates the gathering of the user's attributes, and in FIG. 5, which illustrates the data processing and transmission of the attributes.

FIG. 3 illustrates the events that take place in user registration. The user can register via the monitor device 210 or any computing machine that enables communication to the processing unit 510. The user logs-in and account registration is initiated 3000 if user has not registered. The user provides account information (e.g. name, address, date of birth, prior medical history, or monitor device serial number). The user then creates 3100 a profile, which is a set of data relating to a specific service (e.g. monitoring the blood glucose level or monitoring alcohol level) by selecting 3200 the type of service needed such as analyte measurement reading, analysis and tracking of physiological and behavioral attributes, transmitting information among information recipients, or any combination of the above mentioned services. After service is selected 3200, the user selects one or more physiological attributes to track 3300, one or more analytes to be measured 3400, and one or more behavioral attributes to track 3500. If information transmission among recipients is selected in step 3200, the user needs to input all recipients' information and recipient parameters 3600. The profile is stored in the storage module 214 of the monitor device 210 and in a profile database 516 in the account manger 512 of the processing unit 510. Alternatively, the profile can be stored on either the storage module 214 or the account manger 512. Profile is completed 3700 and the data processing unit sends a confirmation with password to the user and his list of recipients. Alternatively, the user can create numerous profiles within the same account.

After user registration, the user can utilize his device to gather physiological and behavioral attributes, which is illustrated in FIG. 4. The user logs-in 4000 to the device 210 with password from the registration and user account is presented by the input module 4100. Alternatively, user log-in can be accomplished by voice recognition or by a fingerprint. The user selects the desired profile 4200. If behavior inputs are required, the user inputs 4300 the behavior attributes such as "time duration between analyte measurement and last meal," "time duration between analyte measurement and last exercise session," "time duration between analyte measurement and last resting session," or "whether other drugs or alcohol was taken prior to measurement." If no behavioral attributes are required, the user is presented with opportunity to select analyte measurement. If selected, the user selects the desired analyte to be measured 4400 and if calibration is needed, the calibrator module is initiated to calibrate 4500 the analyte measurement generator 213. If calibration is complete, the user can place his finger 4600 on the ATR plate and the analyte measurement generator records 4700 and calculates the analyte level. If only the analyte measurement is selected and no processing is needed, the output module 216 of the monitor device 210 will display the measurement. If further processing is required, the data is sent 4800 to the processing unit and the data is processed, as illustrated in more detail in FIG. 5.

In FIG. 5, the data processing unit 510 receives transmission from the monitor device 5100. The user is verified 5200 via the security module and user account is accessed 5300 by the account manager. If the transmission pertains to an existing profile, the data is transferred and the profile database in the account manager is updated 5700. If the transmission consists of data pertaining to a new profile, a new profile is created by the processing unit 5400 and data is transferred 5500. The processing unit then organizes and correlates the data according to the behavioral and physiological relationships and recipient parameters 5600 and updates the profile database in the account manager 5700. After updating the profile database 5700, the account manager is responsible for sending out the corresponding reports and profiles at the corresponding time to each recipient based on the recipient parameters 5800. Alternatively, the reports and profiles are encrypted and access is only granted to recipients with valid passwords to prevent unauthorized use.

Foregoing described embodiments of the invention are provided as illustrations and descriptions. They are not intended to limit the invention to precise form described. In particular, it is contemplated that functional implementation of invention described herein may be implemented equivalently in hardware, software, firmware, and/or other available functional components or building blocks. Other variations and embodiments are possible in light of above teachings, and it is thus intended that the scope of invention not be limited by this Detailed Description, but rather by Claims following.

We claim:

1. A method for implementing a patient monitor program for a user by a service provider, the method comprising the steps of:

recording a physiological attribute of a patient on a device, wherein the device utilizes attenuated total reflection (ATR) infrared spectroscopy to record the attribute; and sending the attribute to one or more users via a network.

2. The method of claim 1, wherein the attribute is blood glucose level.

3. The method of claim 1, wherein the attribute is a blood analyte level.

4. The method of claim 1, further comprising the step of processing one or more attribute to generate a profile of the patient.

5. The method of claim 1, further comprising the step of correlating the physiological attributes with the behavioral attributes in generating the profile of the patient.

6. The method of claim 5, further comprising the step of encrypting the profile to protect unauthorized access.

7. The method of claim 1, further comprising the step of transmitting the attribute wirelessly.

8. The method of claim 7, wherein the wireless transmission is performed via coupling the device to a cellular phone.

9. The method of claim 7, wherein the wireless transmission is performed via coupling the device to a wireless transmitting device.

10. The method of claim 1, wherein the attribute is transmitted to a local processing unit over a short range radio frequency (RF) link.

11. The method of claim 10, wherein Blue tooth protocol is utilized in the transmission.

12. A patient monitor system to enable sharing of information among information recipients comprising:

an input device to record an attribute of an patient, wherein the device utilizes attenuated total reflection (ATR) infrared spectroscopy to record the attribute; and a data processing unit to process the attributes to generate and transmit a profile of the patient to a recipient.

13. The system of claim 12, wherein the profile is transmitted via a network.

14. The system of claim 12, wherein the profile is transmitted wirelessly.

15. The system of claim 12, wherein the profile is transmitted based on recipient parameters.

16. The system of claim 12, further comprises a security module to verify recipient access to profiles.

17. A method of transmitting an analyte measurement from an input device to a user output device comprising the steps of:

contacting a skin surface of a patient to an ATR plate in said input device;

recording an analyte level measurement in the skin via ATR infrared spectroscopy; and transmitting said analyte level measurement to one or more user.

18. The method of claim 17, wherein said measurement is transmitted via a network.

19. The method of claim 18, wherein said network is the Internet.

20. The method of claim 17, wherein said measurement is transmitted via a wireless protocol.

21. The method of claim 20, wherein said wireless transmission is performed via coupling the input device to a cellular phone.

22. The method of claim 20, wherein said wireless transmission is performed via coupling the input device to a pager.

23. The method of claim 20, wherein said input device contains a wireless transmission module.

24. The method of claim 17, further comprising the step of restricting user access by a pre-determined rule set.

25. The method of claim 17, further comprising the step of processing the analyte measurement to generate a profile.

26. The method of claim 25, wherein the processing relates to correlating said analyte measurement with behavioral attributes of the patient.

27. The method of claim 17, wherein the analyte measurement is blood glucose level.

\* \* \* \* \*